United States Patent
Han et al.

(10) Patent No.: US 7,722,751 B2
(45) Date of Patent: May 25, 2010

(54) APPARATUS FOR REGULATING SALT CONCENTRATION USING ELECTRODIALYSIS, LAB-ON-A-CHIP INCLUDING THE SAME, AND METHOD OF REGULATING SALT CONCENTRATION USING THE APPARATUS

(75) Inventors: Jung-im Han, Seoul (KR); Young-sun Lee, Seongnam-si (KR); Joon-ho Kim, Seongnam-si (KR)

(73) Assignee: Samsung Electronics Co., Ltd. (KR)

( * ) Notice: Subject to any disclaimer, the term of this patent is extended or adjusted under 35 U.S.C. 154(b) by 1035 days.

(21) Appl. No.: 11/440,872

(22) Filed: May 25, 2006

(65) Prior Publication Data

US 2006/0266650 A1      Nov. 30, 2006

(30) Foreign Application Priority Data

May 25, 2005    (KR)  .................. 10-2005-0044250

(51) Int. Cl.
*B01D 61/48* (2006.01)
(52) U.S. Cl. .................. 204/522; 204/527; 204/529; 204/530; 204/540; 204/633
(58) Field of Classification Search ............. 204/522, 204/527, 529, 530, 540, 633
See application file for complete search history.

(56) References Cited

U.S. PATENT DOCUMENTS 4,594,135 A * 6/1986 Goldstein .............. 204/551
4,702,810 A 10/1987 Kunz
6,284,117 B1 * 9/2001 Smolko et al. .............. 204/543

FOREIGN PATENT DOCUMENTS

| JP | 55-024924 A | 2/1980 |
|---|---|---|
| JP | 02-009493 A | 1/1990 |
| JP | 07-163845 A | 6/1995 |
| JP | 2003-190959 A | 7/2003 |
| WO | 9718503 A1 | 5/1997 |

* cited by examiner

*Primary Examiner*—Arun S Phasge
(74) *Attorney, Agent, or Firm*—Cantor Colburn LLP (57) ABSTRACT

An apparatus for regulating salt concentration, a lab-on-a-chip including the same and a method of regulating salt concentration using the apparatus are provided. The apparatus includes: a reaction chamber that is defined by a cation exchange membrane and an anion exchange membrane and is selected from the group consisting of a biomolecule extraction chamber, an amplification chamber, a hybridization chamber, and a detection chamber; a first electrode chamber that is defined by the anion exchange membrane and a first electrode and includes an ion exchange medium; and a second electrode chamber that is defined by the cation exchange membrane and a second electrode and includes an ion exchange medium. Even without injecting solutions with different salt concentrations into the reaction chamber by operating pumps and valves for each operation stage, the salt concentration can be reversibly regulated in situ by adjusting the polarity, intensity and application time of a voltage.

10 Claims, 9 Drawing Sheets

SEQUENCE LISTING

```
<160> NUMBER OF SEQ ID NOS: 2

<210> SEQ ID NO 1
<211> LENGTH: 19
<212> TYPE: DNA
<213> ORGANISM: Artificial Sequence
<220> FEATURE:
<223> OTHER INFORMATION: probe

<400> SEQUENCE: 1
atgacaatga gtatgccta                                                19

<210> SEQ ID NO 2
<211> LENGTH: 19
<212> TYPE: DNA
<213> ORGANISM: Artificial Sequence
<220> FEATURE:
<223> OTHER INFORMATION: target DNA

<400> SEQUENCE: 2
tactgttact catacggat                                                19
```

APPARATUS FOR REGULATING SALT CONCENTRATION USING ELECTRODIALYSIS, LAB-ON-A-CHIP INCLUDING THE SAME, AND METHOD OF REGULATING SALT CONCENTRATION USING THE APPARATUS

CROSS-REFERENCE TO RELATED PATENT APPLICATION

This application claims the benefit of Korean Patent Application No. 10-2005-0044250, filed on May 25, 2005, in the Korean Intellectual Property Office, the disclosure of which is incorporated herein in its entirety by reference.

BACKGROUND OF THE INVENTION

1. Field of the Invention

The present invention relates to an apparatus for regulating salt concentration using electrodialysis, a lab-on-a-chip including the same and a method of regulating salt concentration using the apparatus for regulating salt concentration.

2. Description of the Related Art

Due to recent developments in biotechnology, protein sequences and base pair sequences containing genetic information of individuals have been identified. Thus, many researchers have attempted to develop biochips, particularly, labs-on-chips, for analyzing base pair sequences, diagnosing diseases, etc.

A lab-on-a-chip is an automated and micronized chip that can process the following experimental procedures in situ: extracting a biomolecule such as deoxyribonucleic acid (DNA), ribonucleic acid (RNA) or a protein from a sample containing cells; amplifying the extracted biomolecule; hybridizing the amplified biomolecule to a previously immobilized biomolecule; detecting the hybridized result; and providing quantitative analysis of the experimental results.

Generally, a lab-on-a-chip includes: an extraction chamber in which a biomolecule is extracted; an amplification chamber in which the extracted biomolecule is amplified; a hybridization chamber in which the amplified biomolecule is hybridized to biomolecules immobilized in the hybridization chamber; a detection chamber in which whether hybridisation has occurred or not is detected; and micro-channels connecting the above-described chambers. In the extraction chamber, cells in a sample are enriched and lysed to purify a biomolecule therefrom. In the amplification chamber, a biomolecule is amplified through, for example, a polymerase chain reaction (PCR). A biomolecule with known base pair sequences is immobilized on a side of the hybridization chamber, and hybridization between the immobilized biomolecule and the amplified biomolecule occurs in the hybridization chamber. The degree of the hybridization is measured in the detection chamber.

The lab-on-a-chip requires different salt concentrations at each operation stage, including an enrichment stage, a lysis stage, a purification stage, an amplification stage, a hybridization stage, a washing stage, a drying stage, and a detection stage. Therefore, solutions with different salt concentrations are previously prepared and then injected individually into each operation chamber. Alternatively, when the operation stages are carried out in one chamber, solutions with different salt concentrations are injected for each operation stage.

Figure 1:
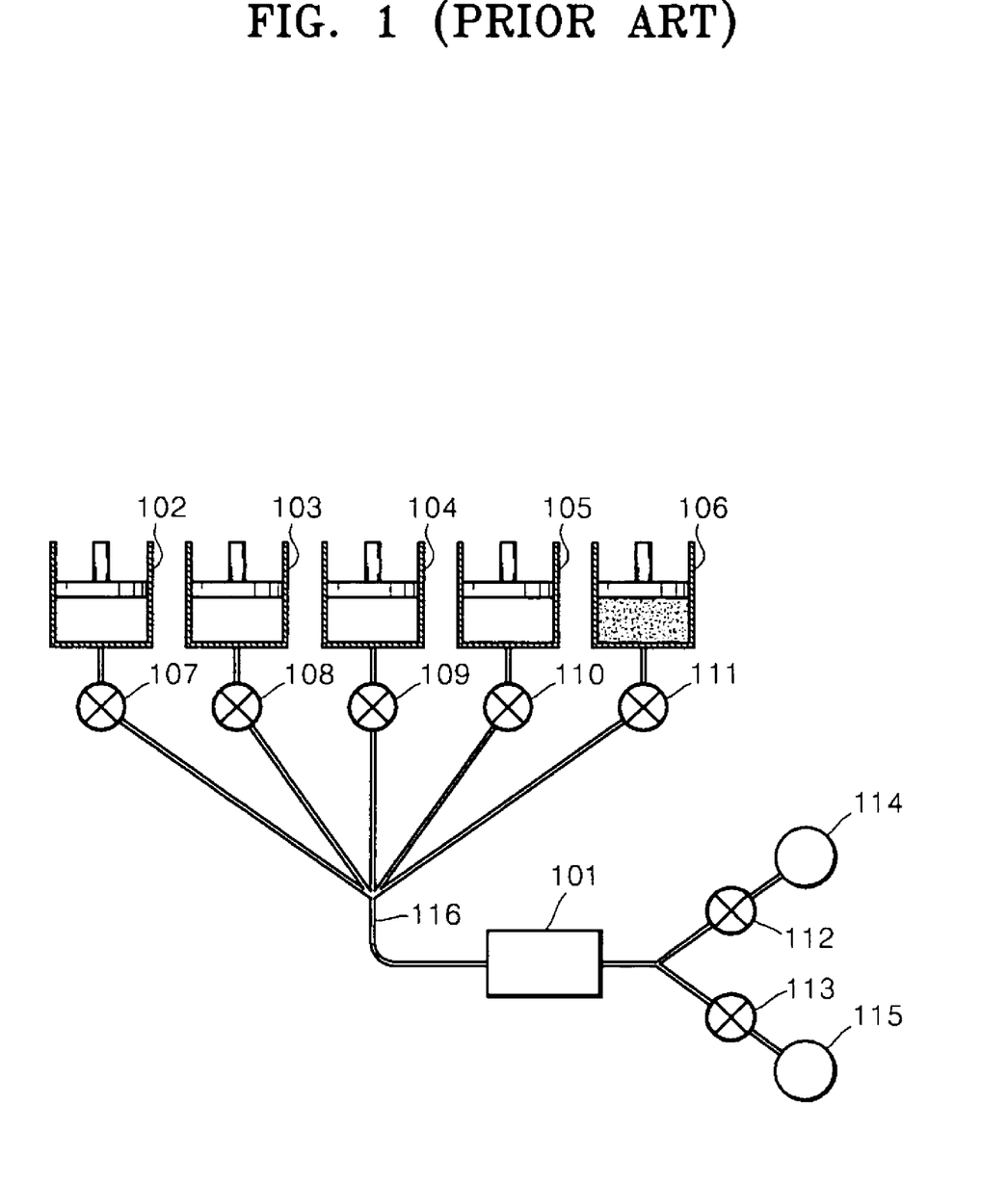
FIG. 1 illustrates a conventional apparatus for injecting solutions with different salt concentrations into a reaction chamber.

FIG. 1 illustrates a conventional apparatus for injecting solutions with different salt concentrations into a reaction chamber 101 of a lab-on-a-chip.

Referring to FIG. 1, the reaction chamber 101 where each reaction such as hybridization takes place is connected to first through fifth pumps 102, 103, 104, 105, and 106 through a channel 116. The first pump 102 pumps a washing buffer solution. The second through fourth pumps 103, 104 and 105 pump solutions with different salt concentrations. The fifth pump 106 pumps a sample solution with a biomolecule. The washing buffer solution, which does not include salt, and the solutions with the different salt concentrations are injected into the reaction chamber 101 by adjusting the flow from the first through fifth pumps 102, 103, 104, 105, and 106 with first through fifth valves 107, 108, 109, 110, and 111. The used solutions are discharged into storage units 114 and 115 by adjusting a sixth valve 112 and a seventh valve 113.

However, the above described conventional apparatus needs many parts including the pumps, the valves, the channel, and the storage units, and thus, the apparatus may be complicated. For each operation stage, the pumps and the valves are operated to inject and discharge each solution. Hence, an operation time may be long.

SUMMARY OF THE INVENTION

As a result of continuous research, the inventors of the present invention have found that the salt concentration of a solution can be regulated in situ through electrodialysis using cation and anion exchange membranes by changing the polarity of a voltage applied to an electrode, without supplying solutions with different salt concentrations by operating pumps and valves for each operation stage, and completed the present invention.

The present invention provides an apparatus for regulating salt concentration in situ.

The present invention also provides a lab-on-a-chip including the apparatus for regulating salt concentration in situ.

The present invention further provides a method of regulating the salt concentration of a solution within a reaction chamber using the apparatus for regulating salt concentration in situ.

According to an aspect of the present invention, there is provided an apparatus for regulating salt concentration, comprising: a reaction chamber that is defined by a cation exchange membrane and an anion exchange membrane and is selected from the group consisting of a biomolecule extraction chamber, an amplification chamber, a hybridization chamber, and a detection chamber; a first electrode chamber that is defined by the anion exchange membrane and a first electrode and includes an ion exchange medium; and a second electrode chamber that is defined by the cation exchange membrane and a second electrode and includes an ion exchange medium.

According to another aspect of the present invention, there is provided a lab-on-a-chip including the above-described apparatus for regulating salt concentration.

According to a further aspect of the present invention, there is provided a method of regulating salt concentration, the method comprising: injecting a sample solution including a biomolecule into the reaction chamber of the above-described apparatus for regulating salt concentration; applying a voltage with a first polarity between the first electrode and the second electrode; and applying a voltage with a second polarity opposite to the first polarity between the first electrode and the second electrode.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

The present invention will be described more fully hereinafter with reference to the accompanying drawings in which certain embodiments of the invention are shown.

Figure 2:
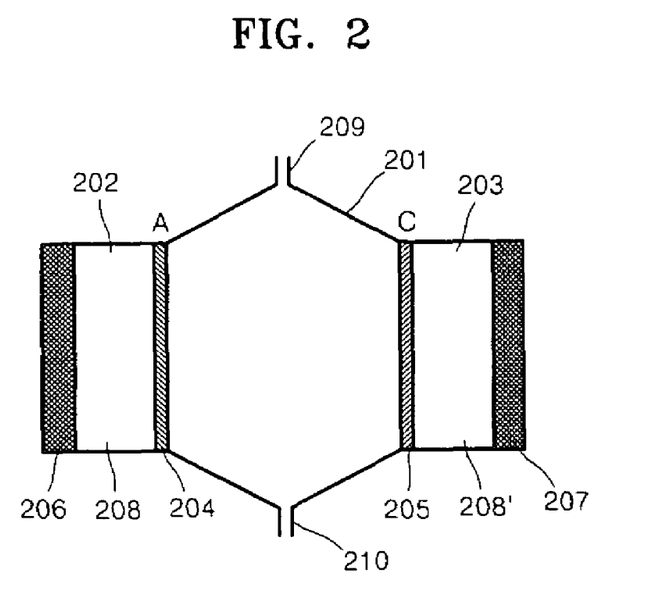
FIG. 2 is a cross-sectional view of an apparatus for regulating a salt concentration according to an embodiment of the present invention.

FIG. 2 is a cross-sectional view of an apparatus for regulating a salt concentration according to an embodiment of the present invention.

Referring to FIG. 2, the apparatus includes: a reaction chamber 201 defined by an anion exchange membrane 204 and a cation exchange membrane 205; a first electrode chamber 202 defined by the anion exchange membrane 204 and a first electrode 206 and containing a first ion exchange medium 208; and a second electrode chamber 203 defined by the cation exchange membrane 205 and a second electrode 207 and containing a second ion exchange medium 208'

Referring to FIG. 2, in the apparatus according to the present invention, the reaction chamber 201 can further include an inlet 209 into which a sample solution including a biomolecule is injected; and an outlet 210 through which the sample solution is discharged.

Figure 3:
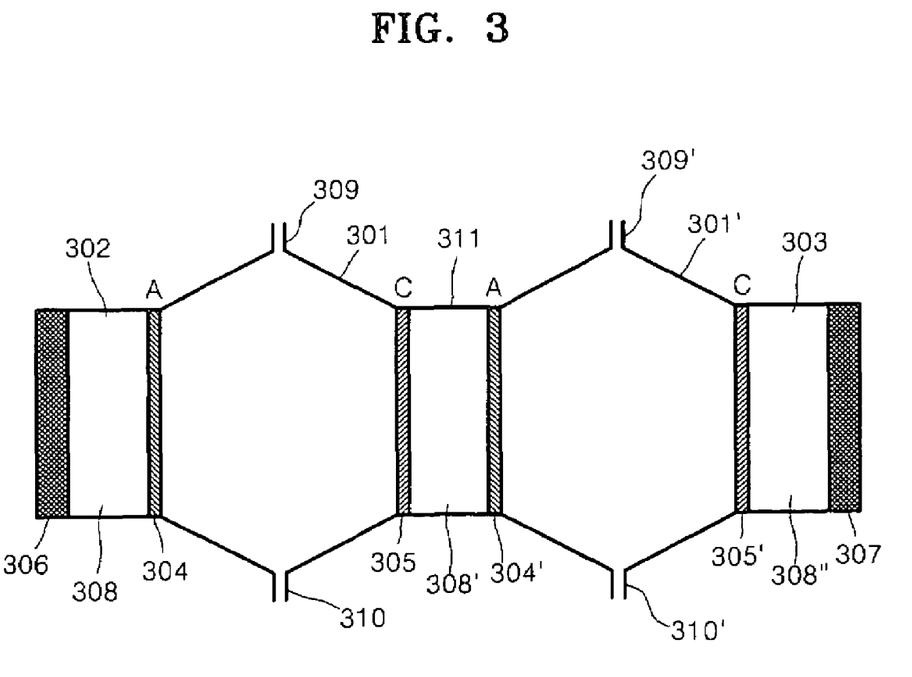
FIG. 3 is a cross-sectional view of an apparatus for regulating a salt concentration according to an embodiment of the present invention.

FIG. 3 is a cross-sectional view of an apparatus for regulating a salt concentration according to another embodiment of the present invention.

Referring to FIG. 3, the apparatus includes: a first reaction chamber 301 defined by a first anion exchange membrane 304 and a first cation exchange membrane 305; a second reaction chamber 301' defined by a second anion exchange membrane 304' and a second cation exchange membrane 305'; an ion chamber 311 defined by the first cation exchange membrane 305 and the second anion exchange membrane 304' and containing a second ion exchange medium 308'; a first electrode chamber 302 defined by the first anion exchange membrane 304 and a first electrode 306 and containing a first ion exchange medium 308; and a second electrode chamber 303 defined by the second cation exchange membrane 305' and a second electrode 307 and containing a third ion exchange medium 308".

The apparatus according to the embodiment illustrated in FIG. 3 has two reaction chambers (i.e., the first reaction chamber 301 and the second reaction chamber 301') and additionally includes the ion chamber 311, which is disposed between the first reaction chamber 301 and the second reaction chamber 302, is defined by the first cation exchange membrane 305 and the second anion exchange membrane 304', and contains the second ion exchange medium 308'.

Referring to FIG. 3, in the apparatus for regulating a salt concentration according to the present invention, the first reaction chamber 301 can further include a first inlet 309 into which a sample solution is injected, and a first outlet 310 through which the sample solution is discharged. The second reaction chamber 301' can further include a second inlet 309' into which a sample solution is injected; and a second outlet 310' through which the sample solution is discharged.

In the apparatuses for regulating a salt concentration in FIGS. 2 and 3, the reaction chamber can be selected from the group consisting of an extraction chamber, an amplification chamber, a hybridization chamber, and a detection chamber. Alternatively, the reaction chamber can be an integrated chamber which can function as a extraction chamber, a amplification chamber, a hybridization chamber, and a detection chamber.

When the reaction chamber is a hybridization chamber, a biomolecule is hybridized in the reaction chamber. To this end, a biomolecule selected from the group consisting of deoxyribonucleic acid (DNA), ribonucleic acid (RNA), peptide nucleic acid (PNA), locked nucleic acid (LNA), a peptide, and a protein is immobilized on a substrate of the reaction chamber. A sample solution including a biomolecule selected from the group consisting of DNA, RNA, a peptide, and a protein is injected into the reaction chamber. The substrate can be composed of a material selected from the group consisting of a silicon wafer, glass, metal, and a plastic material, and can be coated with an active group selected from the group consisting of aminosilane, poly-L-lysine, and aldehyde.

In the apparatus for regulating a salt concentration in FIG. 2, the cation exchange membrane 205 allows cations to pass and exhibits nearly 100% resistance to the passage of anions. On the other hand, the anion exchange membrane 204 allows anions to pass and exhibits nearly 100% resistance to the passage of cations. The cation exchange membrane 205 and the anion exchange membrane 204 are well known to and can be easily purchased and used by those skilled in the art. For instance, the cation exchange membrane 205 can be a strong acid exchange membrane including an ionic group of —$SO_3$—$Na^+$ (Nafion™, DuPont), or a weak acid exchange membrane including an ionic group of —COO—$Na^+$. The anion exchange membrane 204 can be a strong base exchange membrane including an ionic group of —N⁺(CH$_3$)Cl⁻ or a weak base exchange membrane including N(CH$_3$)$_2$.

The apparatus can further include: a pump for injecting a sample solution to the reaction chamber 201; a pump for discharging the sample solution from the reaction chamber 201; and valves for adjusting the injection and discharge of the sample solution. The pump for injecting the sample solution to the reaction chamber 201 can be connected to the inlet 209 through a channel, and the pump for discharging the sample solution from the reaction chamber can be connected to the outlet 210 through a channel.

The first electrode 206 and the second electrode 207 can be connected to a positive electrode and a negative electrode, respectively, or vice versa. That is, the first electrode 206 and the second electrode 207 can be connected to a variable power source in which the polarity of a voltage supply changes.

The concentration of salt in the solution within the reaction chamber 201 can be freely adjusted by applying voltages with different polarities between the first electrode 206 and the second electrode 207. This approach can provide a solution to the problems of a conventional method of performing sequential operations for a cell enrichment stage, a cell lysis stage, a biomolecule purification stage, an amplification stage, and a hybridization stage in each chamber provided with a different salt concentration and a conventional method of injecting solutions with different salt concentrations for each operation stage into one chamber. That is, by adjusting the polarity of the voltage applied between the first electrode 206 and the second electrode 207, the salt concentration in the reaction chamber 201 can be freely regulated without performing each operation stage in a different chamber or without injecting solutions with different salt concentrations for each operation stage.

The first electrode 206 and the second electrode 207 can be composed of a metal selected from the group consisting of platinum, gold, copper, and palladium, but are not limited thereto. The first and second ion exchange media 208 and 208' can be aqueous electrolyte solutions. The aqueous electrolyte solutions are not specifically limited, and those skilled in the art can select appropriate aqueous electrolyte solutions according to reaction characteristics.

The above description of the apparatus of FIG. 2 also applies to the apparatus of FIG. 3.

Hereinafter, a lab-on-a-chip including a salt concentration regulating apparatus according to an embodiment of the present invention will be described in detail.

Using the salt concentration regulating apparatus, a salt concentration necessary for each operation stage can be regulated in one reaction chamber. Thus, the sequential operations of the cell enrichment stage, the cell lysis stage, the biomolecule purification stage, the amplification stage, and the hybridization stage can be performed in one reaction chamber without injecting solutions with different salt concentrations for each operation stage.

Hence, the lab-on-a-chip including the salt concentration regulating apparatus has a simplified structure by having fewer chambers and uses a simplified process since the injection and discharge of the solutions with different salt concentrations for each operation stage is not necessary.

Hereinafter, a method of regulating the salt concentration of a solution within a reaction chamber using the salt concentration regulating apparatus according to an embodiment of the present invention will be described. The method includes: injecting a sample solution including a biomolecule into the reaction chamber; applying a voltage with a first polarity to the first electrode and the second electrode; and applying a voltage with a second polarity opposite to the first polarity to the first electrode and the second electrode.

The biomolecule can be selected from the group consisting of DNA, RNA, a peptide, and a protein. The reaction chamber can be an integrated chamber functioning as an extraction chamber, an amplification chamber, a hybridization chamber, and a detection chamber.

Figure 4A:
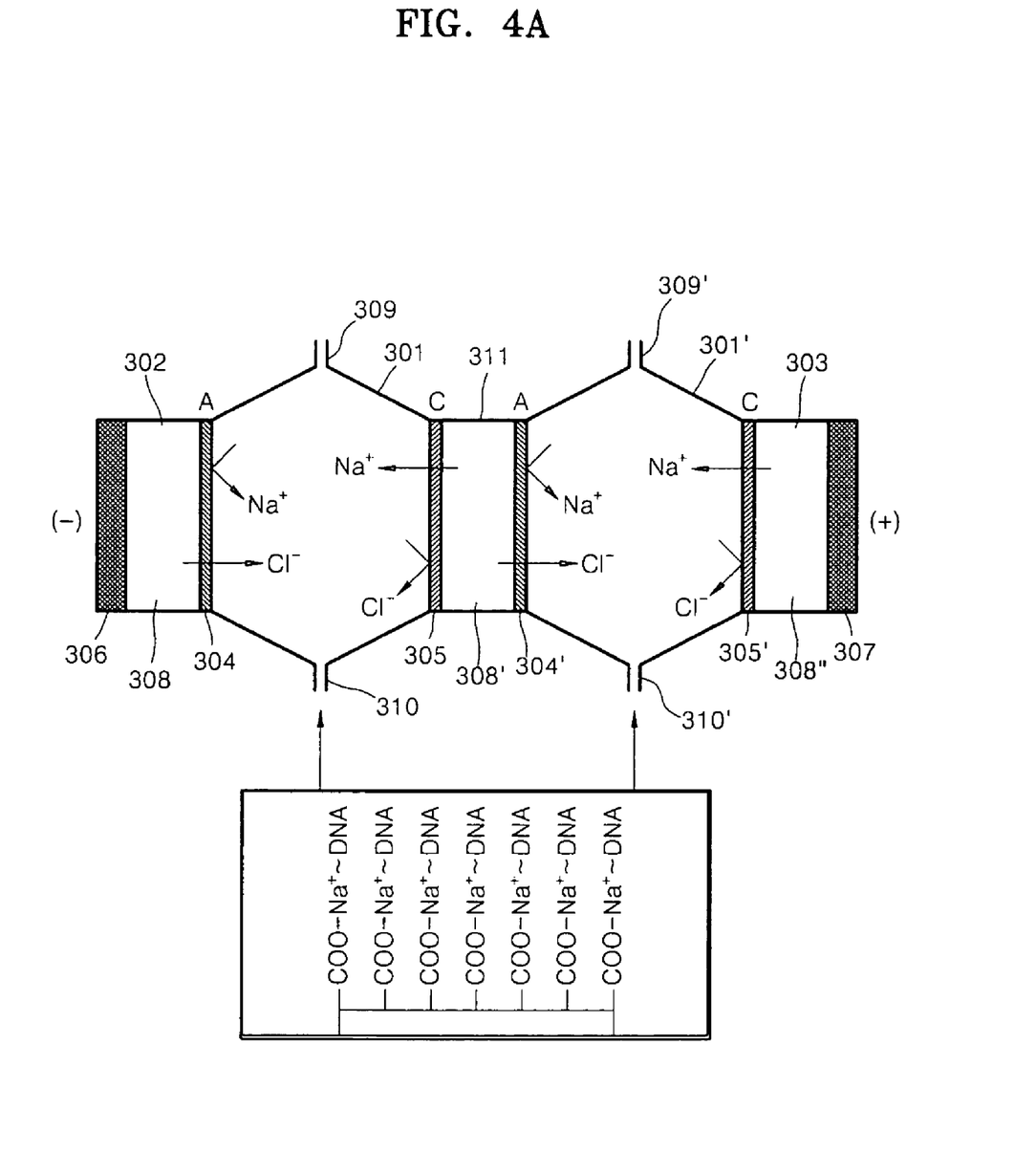
FIGS. 4A and 4B are diagrams illustrating the operation of the apparatus for regulating a salt concentration illustrated in FIG. 3.
Figure 4B:
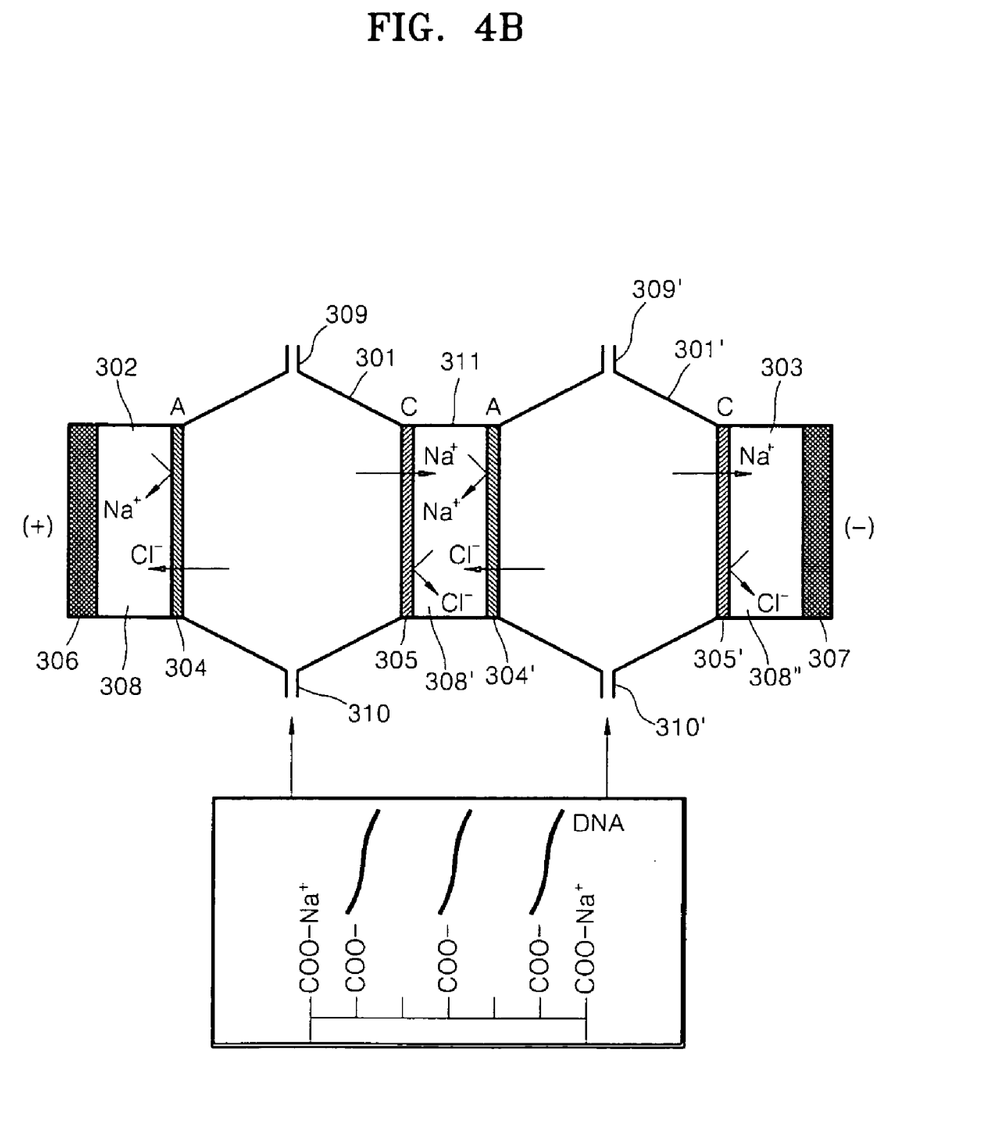

FIGS. 4A and 4B illustrate the operation of the salt concentration regulating apparatus illustrated in FIG. 3. The first through third ion exchange media 308, 308' and 308" are aqueous solutions of sodium chloride.

A sample solution including a biomolecule and a certain amount of salt is injected into the first reaction chamber 301 and the second reaction chamber 301' through a first inlet 309 and a second inlet 309', respectively. The pumps and the valves can control the injection of the sample solution.

Referring to FIG. 4A, a voltage with a first polarity is applied between the first electrode 306 and the second electrode 307. More specifically, a negative voltage is applied to the first electrode 306, and a positive voltage is applied to the second electrode 307. In this case, anions of the first ion exchange medium 308 of the first electrode chamber 302, i.e., chloride ions (Cl⁻), move into the first reaction chamber 301 through the first anion exchange membrane 304, and cations of the second ion exchange medium 308' of the ion chamber 311, i.e., sodium ions (Na⁺), move into the first reaction chamber 301 through the first cation exchange membrane 305. Also, anions of the second ion exchange medium 308', i.e., Cl⁻ ions, move into the second reaction chamber 301' through the second anion exchange membrane 304', and Na⁺ ions of the third ion exchange medium 308" of the second electrode chamber 303 move into the second reaction chamber 301' through the second anion exchange membrane 305'.

However, cations of the sample solution injected into the first reaction chamber 301 and the second reaction chamber 301', i.e., Na⁺ ions, cannot pass through the first anion exchange membrane 304 and the second anion exchange membrane 304', and are thus unable to move into the first electrode chamber 302 and the ion chamber 311. On the other hand, anions of the sample solution injected into the first reaction chamber 301 and the second reaction chamber 301', i.e., Cl⁻ ions, cannot pass through the first cation exchange membrane 305 and the second cation exchange membrane 305', and are thus unable to move into the ion chamber 311 and the second electrode chamber 303.

As a result, the Na⁺ ions and the Cl⁻ ions are concentrated in the first reaction chamber 301 and the second reaction chamber 301' but are diluted in the first electrode chamber 302, the ion chamber 311 and the second electrode chamber 303.

As illustrated in FIG. 4A, when the salt concentration is high, a certain condition, such as the addition of polyethylene glycol (PEG) and DNA, instigates a DNA hybridization reaction.

Referring to FIG. 4B, a voltage with a second polarity opposite to the first polarity is applied between the first electrode 306 and the second electrode 307. That is, a positive voltage is applied to the first electrode 306 and a negative voltage is applied to the second electrode 307. In this case, cations of the sample solution injected into the first reaction chamber 301 and the second reaction chamber 301', i.e., Na⁺ ions, move into the ion chamber 311 and the second electrode chamber 303 through the first cation exchange membrane 305 and the second cation exchange membrane 305', respectively. Also, anions of the sample solution injected into the first reaction chamber 301 and the second reaction chamber 301', i.e., Cl⁻ ions, move into the first electrode chamber 302 and the ion chamber 311 through the first anion exchange membrane 304 and the second anion exchange membrane 304', respectively.

Cations of the first ion exchange medium 308 and the second ion exchange medium 308', i.e., $Na^+$ ions, cannot pass through the first anion exchange membrane 304 and the second anion exchange membrane 304', and are thus unable to move into the first reaction chamber 301 and the second reaction chamber 301'. Also, anions of the second ion exchange medium 308' and the third ion exchange medium 308", i.e., $Cl^-$ ions, cannot pass through the first cation exchange membrane 305 and the second cation exchange membrane 305', and are thus unable to move into the first reaction chamber 301 and the second reaction chamber 301'.

As a result, $Na^+$ ions and $Cl^-$ ions are concentrated in the first electrode chamber 302, the ion chamber 311 and the second electrode chamber 303, but are diluted in the first reaction chamber 301 and the second reaction chamber 301'.

As illustrated in FIG. 4B, when the salt concentration is low, a DNA elution reaction takes place.

In the method of regulating the salt concentration in the reaction chamber of the lab-on-a-chip according to an embodiment of the present invention, the applying of the voltage with a first polarity and the applying of the voltage with the second polarity can be repeated. The salt concentration in the reaction chamber can be effectively regulated by changing the polarity of the voltage supply.

Whether the salt concentration in the reaction chamber can be effectively regulated using a salt concentration regulating apparatus according to an embodiment of the present invention was confirmed in the following examples. As a result, changes in the salt concentration within the reaction chamber can be reversed by changing the polarity of an applied voltage (refer to FIGS. 5A and 5B). In addition, the salt concentration can be increased or decreased according to a voltage application time (refer to FIGS. 6A and 6B). Also, the salt concentration regulated by the salt concentration regulating apparatus is proportional to a degree of DNA hybridization (refer to FIGS. 7A and 7B) and is inverse proportional to a degree of DNA elution (refer to FIG. 8). In addition, there is no change in pH when the salt concentration in the reaction chamber is regulated by the salt concentration regulating apparatus (refer to FIGS. 9A and 9B).

Hence, the salt concentration can be reversibly regulated in situ while maintaining a consistent pH level by controlling the polarity, intensity and the application time of a voltage using the salt concentration regulating apparatus and method according to the present invention. The required polarity, intensity and application time of the voltage can vary depending on a desired salt concentration level, an electrolyte concentration level and the volume of the reaction chamber. Those skilled in the art can experimentally determine such parameters according to their needs.

Hereinafter, the present invention will be described in greater detail with reference to the following examples. The following examples are for illustrative purposes only and are not intended to limit the scope of the present invention.

Example 1

Change in Salt Concentration According to the Polarity of Voltage

In this example, whether a change in the salt concentration could be reversibily regulated within the reaction chamber by changing the polarity of the applied voltage using a salt concentration regulating apparatus according to the present invention was determined.

The salt concentration regulating apparatus illustrated in FIG. 3 was used in this experiment. FIG. 3 is a cross-sectional view of a salt concentration regulating apparatus according to the present invention described above. Membranes including an ionic group of $—SO_3—Na^+$ were used as the cationic exchange membranes, and a membranes including an ionic group of $N^+(CH_3)_3Cl^-$ were used as the anion exchange membranes. The first electrode and the second electrode were composed of platinum. Each of the first reaction chamber, the second reaction chamber, the first electrode chamber, the second electrode chamber, and the ion chamber had a volume of approximately 10 µl. Approximately 1,000 mM of an aqueous sodium chloride (NaCl) solution was used as the ion exchange media, and a sample solution injected into the reaction chamber was approximately 1,000 mM of an aqueous NaCl solution.

A negative voltage was applied to the first electrode of the salt concentration regulating apparatus, and a positive voltage was applied to the second electrode. The voltage between the first and second electrodes was approximately 5 V. After approximately 0.5 minutes, the polarity of the applied voltage was reversed, and the magnitude of the voltage was maintained constant. After 1 minute, the voltage was again applied with the first polarity. After 1.5 minutes, the voltage was applied with the polarity opposite to the first polarity.

Figure 5A:
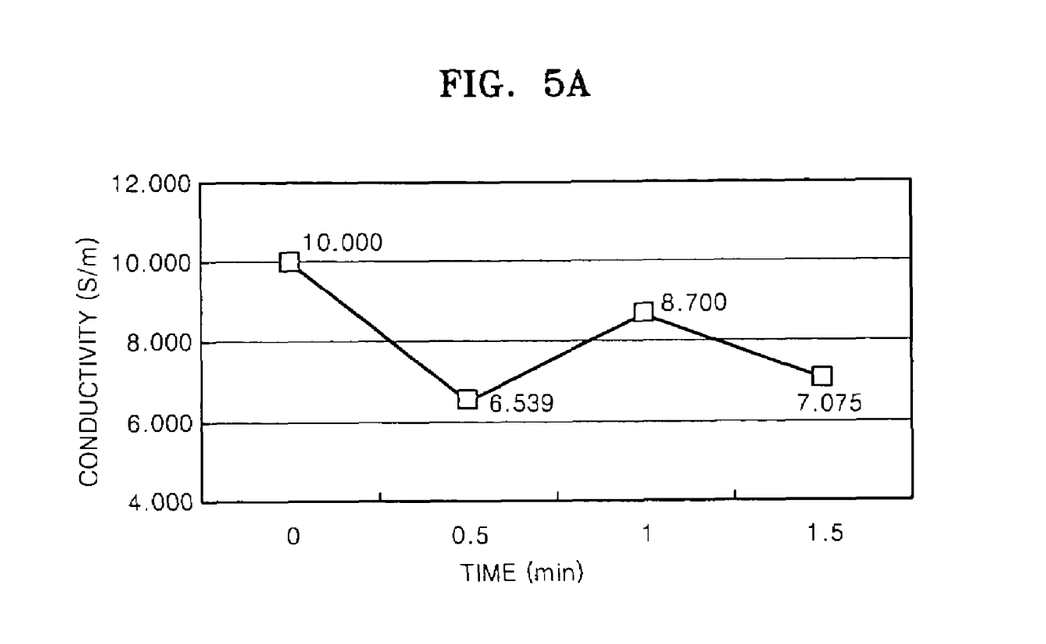
FIG. 5A is a graph illustrating conductivity within a reaction chamber with respect to the polarity of an applied voltage obtained in Example 1 according to the present invention.

A conductivity measuring apparatus (manufactured by Horiba) was used to measure a change in conductivity of the solutions within the reaction chambers. For the conductivity measurement, approximately 10 µl of a sample solution was mixed with deionized water and diluted to obtain an approximately 10 ml solution. Then, a conductivity measurement probe was immersed into the diluted solution. The concentration of NaCl in the solutions of the reaction chambers was measured based on the measured conductivity. The basic principle of this measurement is that the NaCl concentration and conductivity in a measurable large volume, i.e., approximately 10 ml, are proportional. For instance, if the conductivity of the 10 ml solution, which was approximately 1,000 times diluted, was approximately 1 mS/m, the conductivity of the original 10 µl solution could be estimated as approximately 1 S/m. The results are illustrated in FIGS. 5A and 5B.

Figure 5B:
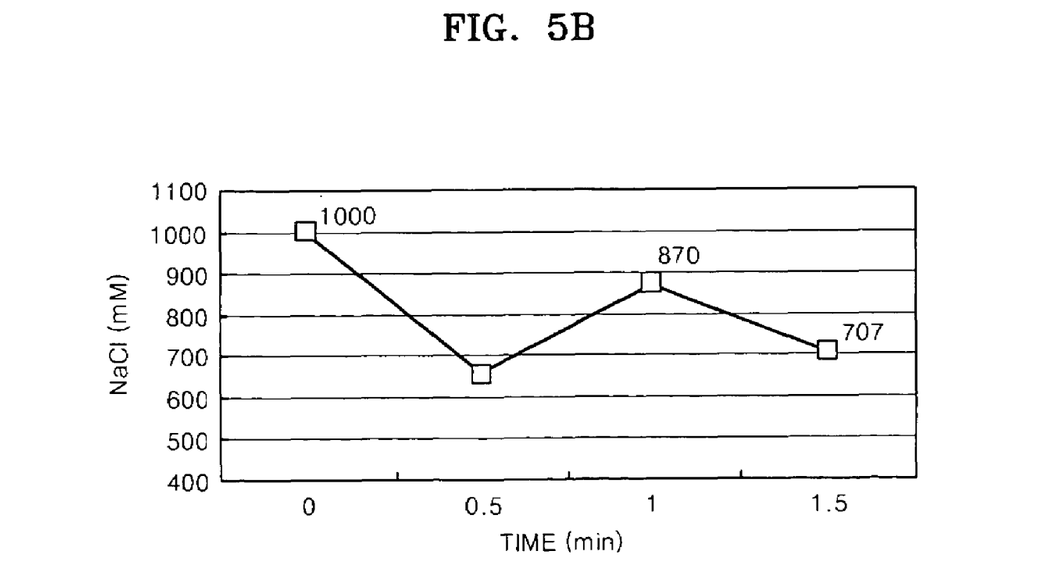
FIG. 5B is a graph illustrating sodium chloride (NaCl) concentration with respect to conductivity illustrated in FIG. 5A.

Referring to FIG. 5B, prior to applying a voltage, the NaCl concentration of the solutions within the reaction chambers was approximately 1,000 mM. When the voltage was applied with a first polarity, the NaCl concentration was decreased to approximately 654 mM after 0.5 minutes. When the voltage was applied with the the polarity opposite to the first polarity, the NaCl concentration was restored to approximately 870 mM after 1 minute. When the voltage was applied again with the first polarity, the NaCl concentration was decreased to approximately 707 mM after 1.5 minutes. These test results indicate that the salt concentration within the reaction chamber could be reversibly regulated by changing the polarity of the voltage applied to the salt concentration regulating apparatus.

Example 2

Change in Salt Concentration According to Time

In this example, a change in the salt concentration within the reaction chamber of a salt concentration regulating apparatus according to time was examined.

The same salt concentration regulating apparatus as in Example 1 was used. As in Example 1, approximately 5 V was applied to the salt concentration regulating apparatus.

Figure 6A:
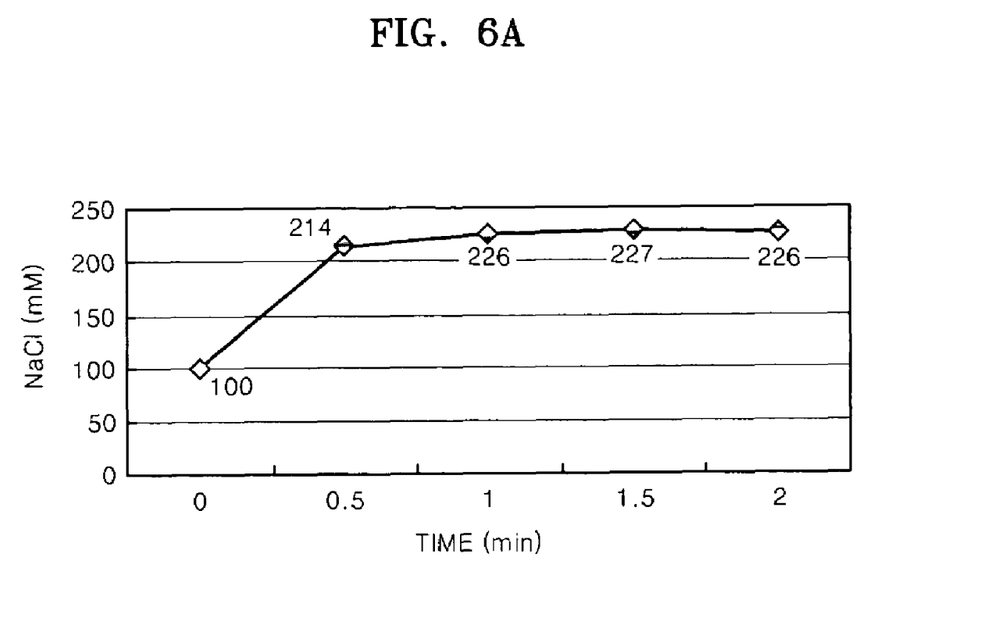
FIGS. 6A and 6B are graphs illustrating the concentration of a NaCl solution within a reaction chamber with respect to time obtained in Example 2 according to the present invention.

In more detail, an aqueous NaCl solution of approximately 100 mM was injected into the reaction chambers. A negative voltage was applied to the first electrode and a positive voltage was applied to the second electrode. Using the same method as in Example 1, the NaCl concentration was measured every 0.5 minutes. The results are shown in FIG. 6A. As time passed, the NaCl concentration increased from approximately 100 mM to approximately 226 mM.

Figure 6B:
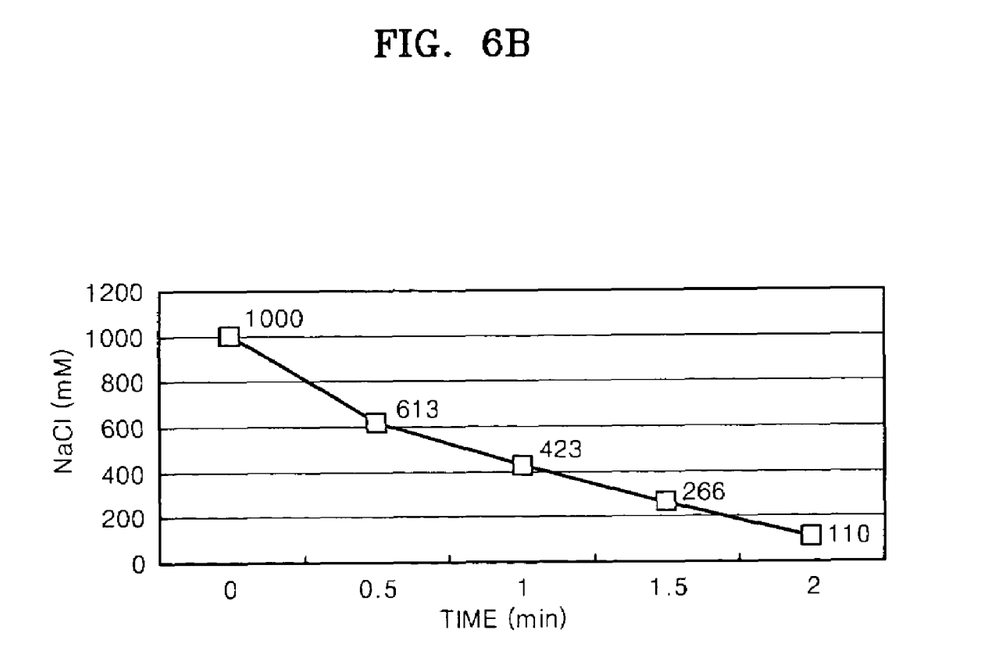

Approximately 1,000 mM of an aqueous NaCl solution was injected into the reaction chambers. A positive voltage was applied to the first electrode and a negative voltage was applied to the second electrode. Using the same method as in Example 1, the NaCl concentration was measured every 0.5 minutes. The results are shown in FIG. 6B. As time passed, the NaCl concentration decreased from approximately 1,000 mM to approximately 110 mM.

The results verified that the salt concentration within the reaction chamber could be regulated using the salt concentration regulating apparatus according to an embodiment of the present invention.

Example 3

Relationship Between Change in Salt Concentration and Degree of DNA Hybridization In this example, it was determined how a change in the salt concentration within the reaction chamber of the salt concentration regulating apparatus affected a degree of DNA hybridization.

A microarray was prepared by immobilizing DNA on a substrate of each reaction chamber of the salt concentration regulating apparatus illustrated in FIG. 3. An N-terminal of a single stranded polynucleotide of SEQUENCE ID NO. 1 was substituted with an amine group and spotted as a probe on a sylated slide (produced by Telechem). At this time, a spotting buffer solution was 2×SSC with a pH of approximately 7. After the spotting, the slide was left in a drier to induce bonding, and washed sequentially with an approximately 0.2% sodium dodecyl sulphate (SDS) solution for approximately 2 minutes and triply-distilled water for approximately 2 minutes to remove non-bonded oligonucleotides. The slide was denatured at approximately 95° C. for approximately 2 minutes, and washed sequentially with a blocking solution for approximately 15 minutes, an approximately 0.2% SDS solution for approximately 1 minute and triply-distilled water for approximately 2 minutes. The blocking solution included approximately 1.0 g of $NaBH_4$, approximately 300 mL of a phosphate buffered saline (PBS) solution with a pH of approximately 7.4 and approximately 100 mL of EtOH. After the washing, the slide was dried, thereby obtaining the microarray.

A single stranded polynucleotide of SEQUENCE ID NO. 2, which could hybridize to the probe immobilized on the substrate, was fluorescently labelled. A hybridization solution including approximately 1 nM of a fluorescently labelled target DNA, 100 mM NaCl, PEG with a molecular weight of approximately 8,000, etc., were injected into a reaction chamber in which the microarray was located to allow hybridization of the fluorescently labelled target DNA to the microarray at approximately 42° C. While performing the hybridization, a negative voltage was applied to the first electrode and a positive voltage was applied to the second electrode. The voltage between the first and second electrodes was approximately 5 V. The slide where the hybridization took place was washed twice with 2×SSC at room temperature for approximately 5 minutes and dried in air. A fluorescence level of the slide was scanned using a Axon GenePix 4000B, and the scanned result was analyzed using a GenePix Pro4.1.

Figure 7A:
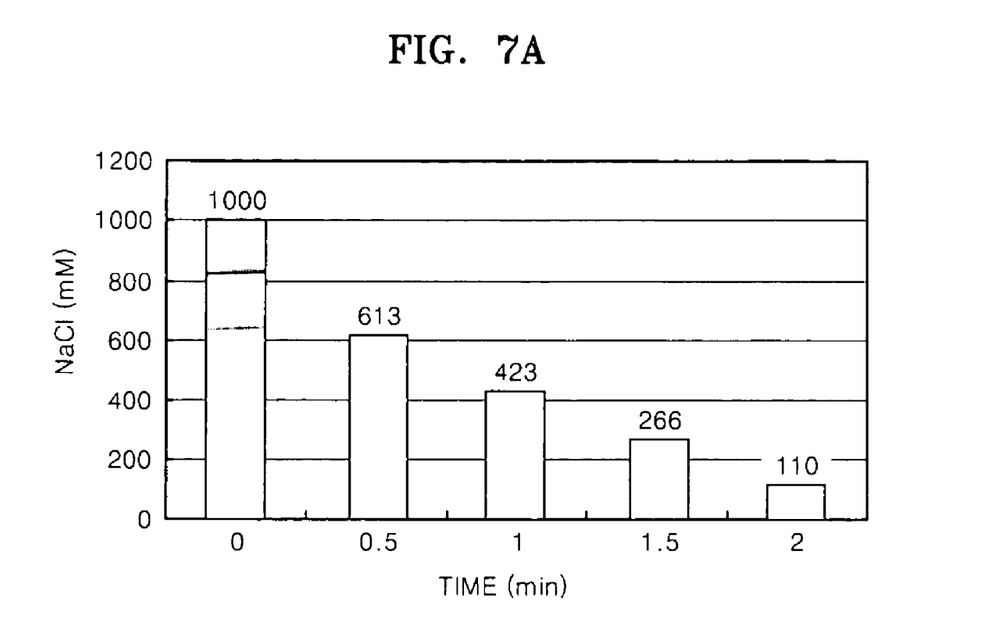
FIG. 7A is a graph illustrating salt concentration within a reaction chamber with respect to time obtained in Example 3 according to the present invention.
Figure 7B:
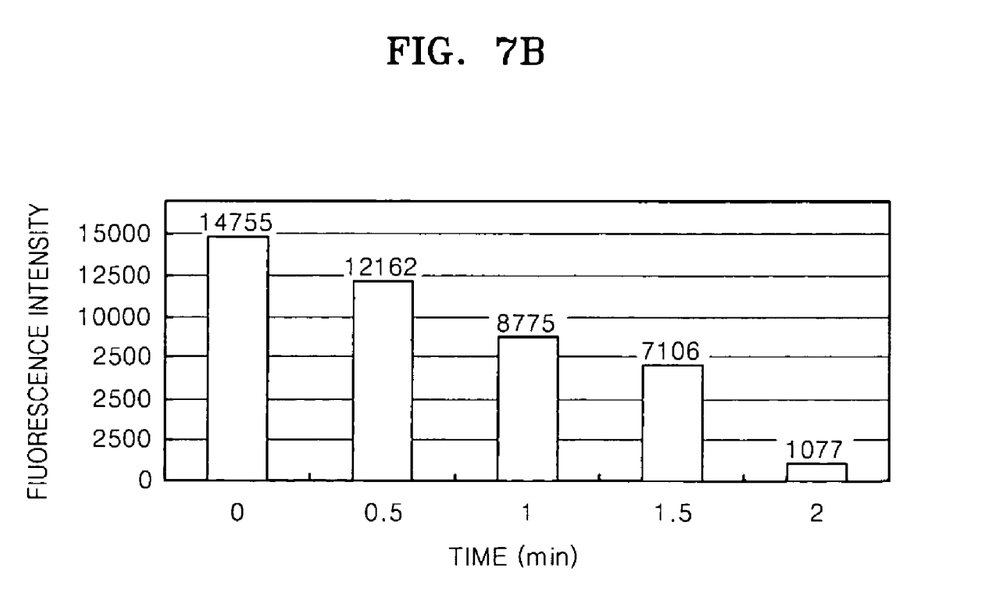
FIG. 7B is a graph illustrating fluorescence intensity, which is proportional to a degree of hybridization, with respect to time obtained in Example 3 according to the present invention.

FIG. 7A illustrates the salt concentration within the reaction chamber with respect to time. FIG. 7B illustrates a fluorescence level proportional to the degree of hybridization within the reaction chamber with respect to time. As illustrated in FIG. 7A, the salt concentration within the reaction chamber at approximately 0 minutes was approximately 1,000 mM, and decreased as time passed. At approximately 2 minutes, the salt concentration was approximately 110 mM. As illustrated in FIG. 7B, the fluorescence level at approximately 0 minutes was approximately 14,755 and decreased as time passed. At approximately 2 minutes, the fluorescence level was approximately 1077. The test results verified that the salt concentration within the reaction chamber and the hybridization degree are proportional.

Example 4

Degree of DNA Elution According to Salt Concentration

In this example, a relationship between the salt concentration within the reaction chamber and a degree of DNA elution was determined.

Figure 8:
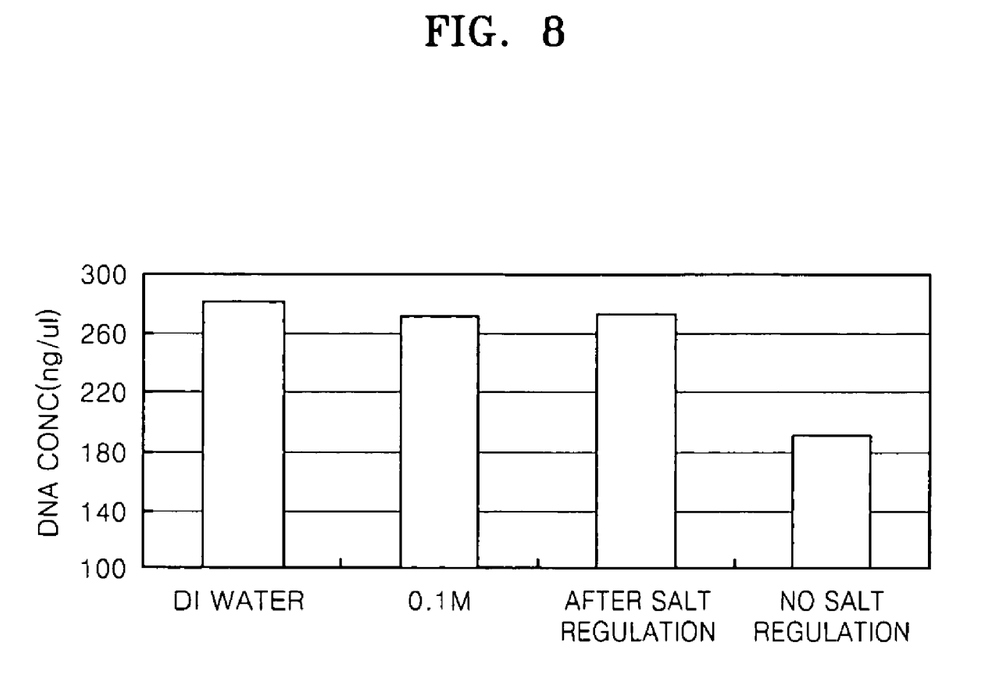
FIG. 8 is a graph illustrating the elution quantity of DNA according to regulation conditions of salt concentration obtained in Example 4 according to the present invention.

A microarray on which DNA was immobilized was manufactured using the method used in Example 3, and pBR 322 was used as DNA. A solution including approximately 20% PEG, approximately 1 M NaCl and approximately 10 µg of pBR 322 was injected into the reaction chambers, and an amount of DNA that was not bonded to the substrate was measured. After the injection, a negative voltage was applied to the first electrode and a positive voltage was applied to the second electrode for approximately 2 minutes. At this time, the voltage between the first and second electrodes was approximately 5 V. The amount of the eluted DNA was measured using ultraviolet (UV) rays. The measurement results are illustrated in FIG. 8. In the case of 'no salt regulation', i.e., when approximately 1 M NaCl was in the reaction chamber and before the voltage was applied, the amount of the eluted DNA was small. In the case of 'after salt regulation', i.e., after the voltage was applied for approximately 2 minutes, the amount of the eluted DNA was nearly identical to a control group in which a salt concentration of approximately 0.1 M was used for the measurement. The case of 'deionized (DI) water' represents the amount of the eluted DNA measured using DI water with a salt concentration of approximately 0.

Example 5

Change in pH According to Time

In this example, a pH level within the reaction chamber was measured with respect to time.

Figure 9A:
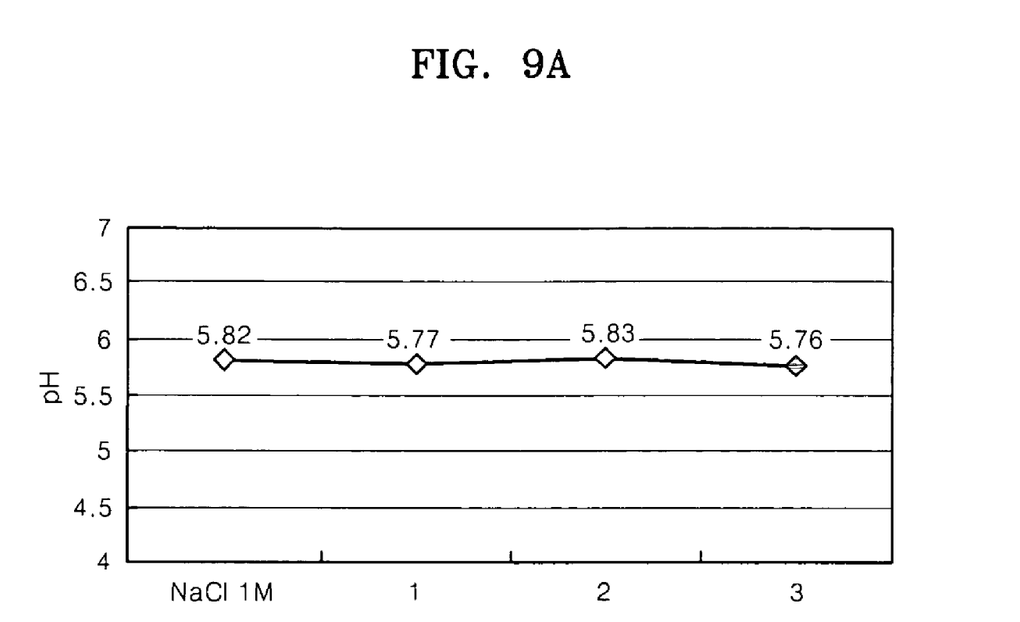
FIGS. 9A and 9B are graphs illustrating pH within a reaction chamber with respect to time obtained in Example 5 according to the present invention.
Figure 9B:
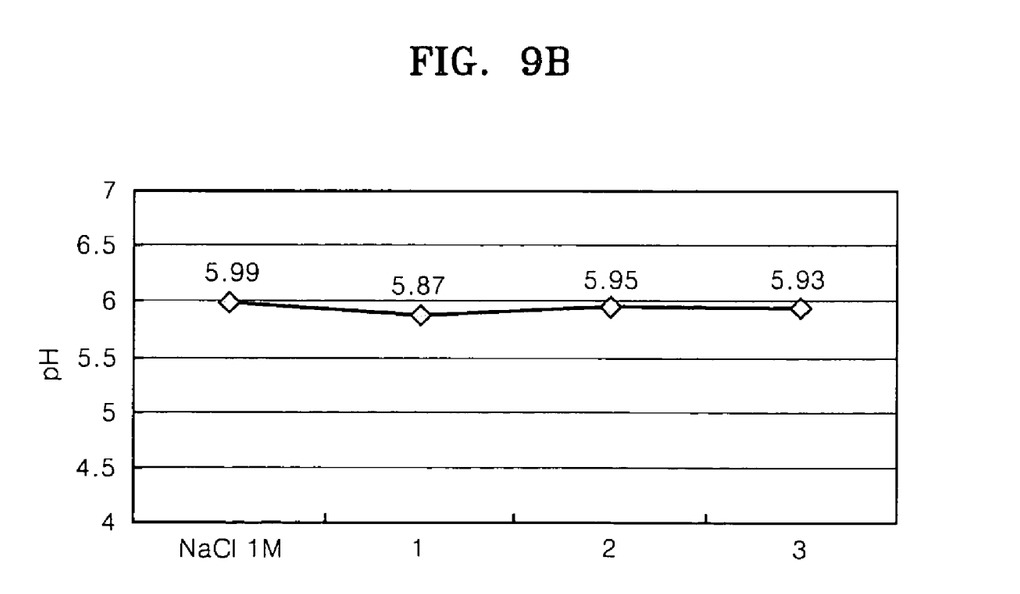

Using the same method as used in Example 2 was used, and, a pH level within the reaction chambers was measured every minute. The measurement results are illustrated in FIGS. 9A and 9B. Particularly, FIGS. 9A and 9B are graphs illustrating pH within the reaction chambers with respect to time. As illustrated in FIGS. 9A and 9B, the pH change was less than approximately 0.1 after approximately 3 minutes. According to the measurement results, free adjustment of the salt concentration and maintenance of a constant pH level were possible using the salt concentration regulating apparatus.

Even without supplying salt solutions with different concentrations by operating pumps and valves for each operation stage, the salt concentration regulating apparatus and method according to various embodiments of the present invention allow the reversible in situ regulation of the salt concentration by adjusting the polarity, intensity and application time of the voltage.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An apparatus for regulating salt concentration, comprising:
   at least two reaction chambers, wherein a reaction chamber is defined by a cation exchange membrane and an anion exchange membrane and is selected from the group consisting of a biomolecule extraction chamber, and amplification chamber, a hybridization chamber, and a detection chamber;
   a first electrode chamber that is defined by the anion exchange membrane and a first electrode and includes an ion exchange medium;
   a second electrode chamber that is defined by the cation exchange membrane and a second electrode and includes an ion exchange medium,
   wherein the first electrode and the second electrode are connected to a variable power source in which the polarity of the voltage supply changes; and
   an ion chamber that is defined by one of the cation exchange membranes and one of the anion exchange membranes defining the at least two reaction chambers, and includes an ion exchange medium.

2. The apparatus of claim 1, wherein the reaction chamber further comprises:
   an inlet into which a sample solution including a biomolecule is injected; and
   an outlet through which the sample solution is discharged.

3. The apparatus of claim 2, wherein the biomolecule is selected from the group consisting of DNA (deoxyribonucleic acid), RNA (ribonucleic acid), a peptide, and a protein.

4. The apparatus of claim 1, wherein the first electrode and the second electrode are applied voltages with different polarities, respectively.

5. The apparatus of claim 1, where in each of the first electrode and the second electrode is composed of a metal selected from the group consisting of platinum, gold, copper, and palladium.

6. The apparatus of claim 1, wherein the ion exchange media are aqueous electrolyte solutions.

7. A lab-on-a-chip comprising the apparatus for regulating salt concentration according to claim 1.

8. A method of regulating salt concentration, the method comprising:
   injecting a sample solution including a biomolecule into the reaction chamber of the apparatus for regulating salt concentration according to claim 1;
   applying a voltage with a first polarity between the first electrode and second electrode; and
   applying a voltage with a second polarity opposite to the first polarity between the first electrode and the second electrode.

9. The method of claim 8, wherein the applying of the voltage with the first polarity and the applying of the voltage with the second polarity are repeated.

10. The method of claim 8, wherein the biomolecule is selected from the group consisting of DNA (deoxyribonucleic acid), ribonucleic acid (RNA), a peptide, and a protein.

* * * * *